United States Patent [19]
Okada

[11] Patent Number: 5,421,726
[45] Date of Patent: Jun. 6, 1995

[54] TOOTH-BRUSHING METHOD BY AN ELECTRIC TOOTHBRUSH HAVING A PREDETERMINED VIBRATION FREQUENCY

[76] Inventor: Eiji Okada, 5-15-5, Nakanobu, Shinagawa-ku, Tokyo, Japan

[21] Appl. No.: 166,453

[22] Filed: Dec. 13, 1993

[30] Foreign Application Priority Data

Mar. 19, 1993 [JP] Japan .................................. 5-85555

[51] Int. Cl.⁶ .............................................. A61C 15/00
[52] U.S. Cl. ..................................... 433/216; 433/122; 15/22.1
[58] Field of Search .................. 433/122, 123, 216; 15/22.1, 22.2; 601/142

[56] References Cited

U.S. PATENT DOCUMENTS

| | | | |
|---|---|---|---|
| 2,187,077 | 1/1940 | Erickson | 15/22.1 |
| 3,183,538 | 5/1965 | Hubner | 601/142 |
| 3,466,689 | 9/1969 | Aurelio et al. | 601/142 |
| 3,535,726 | 10/1970 | Sawyer | 601/142 |
| 3,685,080 | 8/1972 | Hubner | 15/22.1 |

*Primary Examiner*—Cary E. O'Connor
*Attorney, Agent, or Firm*—Flynn, Thiel, Boutell & Tanis

[57] ABSTRACT

A tooth-brushing method comprises the steps of: predeterming respective weights of an electric toothbrush and a heavy eccentric mass as well as a location of the center of gravity of the eccentric mass; establishing an output of a motor at about 7,000 rpm in accordance with the predetermined conditions; and, producing a vibration at about 7,000 rpm by actuating the motor, thereby brushing the teeth.

1 Claim, 3 Drawing Sheets

TOOTH-BRUSHING METHOD BY AN ELECTRIC TOOTHBRUSH HAVING A PREDETERMINED VIBRATION FREQUENCY

FIELD OF THE INVENTION

This invention relates to a tooth-brushing method by means of an electric toothbrush having a predetermined vibration frequency. More precisely, this invention relates to such a tooth-brushing method in which a vibrating tooth-brush has a heavy eccentric weight attached to an electrically operated motor so as to convert a revolving force from the motor into a circular motion which is used to brush the teeth, with bristles on a brush portion of the toothbrush being held in contact with tooth surfaces.

BACKGROUND OF THE INVENTION

Toothbrushes are of the following types: a commonly used toothbrush, which has a handle portion and a brush portion formed integrally so as to be manually operated; and, an electric toothbrush housing an electrically operated motor which is driven by a current flowing from a dry battery or a receptacle.

Tooth-brushing methods using toothbrushes include a bath process, a rolling process, a forns process, a scrapping process, and the like. In accordance with the bath process, bristles on the brush portion are driven in short and quick movements, while being held in contact with the teeth and the gums at about a 45° angle. In the rolling process, the handle portion of the toothbrush is pivoted about an axial direction of the handle portion with a flick of the wrist, thereby causing the brush portion to be pivoted in synchronism therewith. In the forns process, while the toothbrush is held against the teeth at a right angle, the bristles on the brush portion are forced into movement such as to draw a circle. In the scrapping process, while tips of the bristles on the brush portion of the toothbrush are held in contact with the teeth at a right angle, the bristles on the brush portion are driven in short and quick movements.

Although the tooth-brushing methods vary from user to user depending on such factors as the tooth rows and brushing habits of the user as well as the types or extent of periodontal ailments, the methods can broadly be classified into the above four categories.

In some schools, the dental profession educates pupils about brushing of the teeth as a part of educational programs. This system teaches them proper tooth-brushing methods in order to provide dental hygiene management or cure in accordance with states of the teeth.

The electric toothbrush has been developed so as to require less time for brushing the teeth and to afford improved convenience of use, compared with the manually operated toothbrush.

Further, in the electric toothbrush, there is one type in which a revolving force imparted from an electrically operated motor housed therein is converted into, for example, a rolling or otherwise sliding motion by a revolving force-converting mechanism. As another type of electric toothbrush, there is a vibrating toothbrush in which an eccentric heavy weight is attached to the electrically operated motor. These electric toothbrushes are designed to massage the gums as well as brushing tooth surfaces, with the brush portion being held against the teeth, thereby serving as a hygienic instrument for protecting the teeth and the gums from any ailments.

Moreover, the electric toothbrush is usually constructed to allow the brush portion to be removed with respect to the handle portion, so that the brush portion is replaceable when deformations and the like of the bristles on the brush portion over many years of use detract from the ability of the bristles.

In view of conventional manual-operated toothbrushes, different brushing methods can be practiced using a single toothbrush according to the different manner in which the toothbrush is held or moved. However, the action of brushing the teeth must be sustained more than 20 minutes in accordance with a proper tooth-cleaning process in order to secure sufficient cleaning effectiveness. This is inconvenient for brushing because of such a considerable period of time.

Meanwhile, electric toothbrushes are constructed to require less time for brushing than the manually operated toothbrushes, in consideration of respective movements dictated by, for example, the rolling process and/or the bath process, to be specific, one of the movement by the rolling process and the movement by the bath process, or otherwise a changeover between the former and the latter.

In conventional types of vibrating electric toothbrushes, a vibration frequency has usually been established within a limit of about 2,000 to about 3,000 rpm. However, inconveniences arise because the vibration ranging from about 2,000 and about 3,000 rpm produces a feeling of less comfort during brushing, as shown in FIG. 6. This is disadvantageous in practical use, and only insufficient cleaning effectiveness can be obtained.

Another inconvenience arises when the vibration frequency of the electric toothbrush is set at a prescribed value, for example, more than 8,000 rpm. That is, although this setting ensures sufficient cleaning effectiveness, a curve indicative of comfort, as shown in FIG. 6, will be advanced from a region of comfort to a region of discomfort. This is disadvantageous in practical use because of a consequential increase in an uncomfortable feeling during brushing.

In order to eliminate the above-described disadvantages, there is provided a tooth-brushing method according to the present invention by means of an electric toothbrush including a handle portion, an electrically operated motor built in the handle portion, a brush portion held in engagement with the handle portion, and a heavy eccentric mass designed to produce vibration upon actuation of the motor, wherein the motor is actuated to bring the brush portion into vibration so that brushing is practiced through the aid of the vibration, the tooth-brushing method comprising the steps of: predetermining respective weights of the electric toothbrush and the eccentric heavy mass as well as an eccentric location of the center of gravity of the eccentric heavy mass; establishing and output of the motor within a range of about 6,000 to about 8,000 rpm in accordance with the predetermined conditions; producing a vibration ranging from about 6,000 to about 8,000 rpm by actuating the motor; conducting the vibration to tips of bristles on the brush portion, and increasing a pressing force acting along an axial direction of the bristles by the use of a minute circular motion which is produced by the vibration in a plane perpendicular to an axial direction of the brush portion; and brushing the teeth by utilizing the increased pressing force.

In accordance with the present invention as described above, tooth brushing is practiced by means of the electric toothbrush which is constructed to produce a vibration within the range of about 6,000 to about 8,000 rpm. To this end, the vibration in the above range produced by the actuation of the electrically operated motor is conducted to the tips of the bristles on the brush portion. A pressing force acting along the axial direction of the bristles is increased by the minute circular motion which is produced by the vibration in the plane perpendicular to the axial direction of the brush portion. This process ensures a high level of comfort and sufficient tooth-cleaning effectiveness as a result of the above vibration frequency.

DETAILED DESCRIPTION

Figure 1:
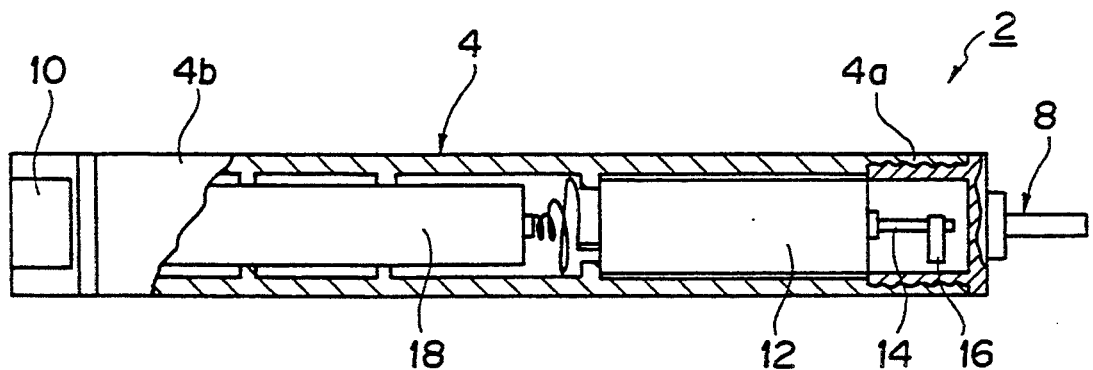
FIG. 1 is a schematic enlarged cross-sectional view showing an inner structure of an electric toothbrush in accordance with an embodiment of the present invention.
Figure 2:
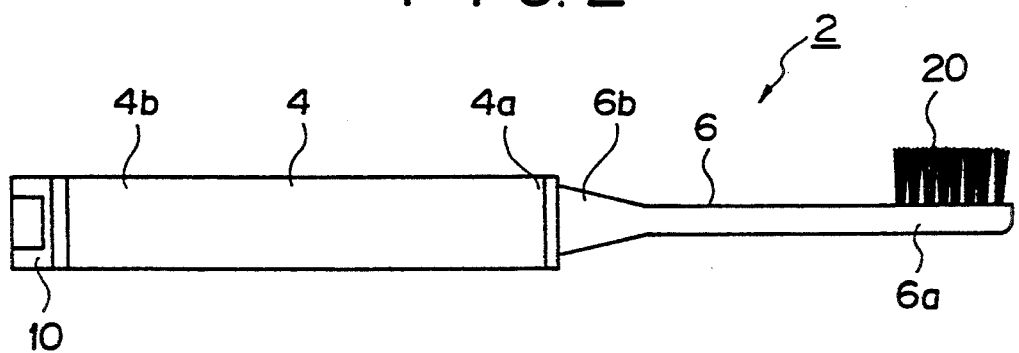
FIG. 2 is a schematic view showing the electric toothbrush.
Figure 3:
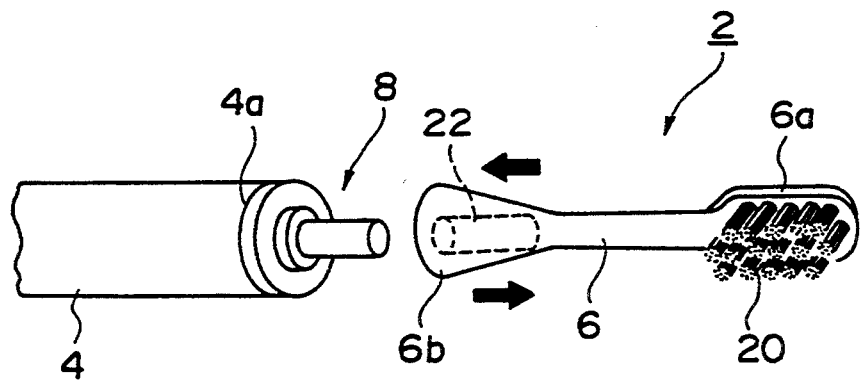
FIG. 3 is a schematic perspective view showing how a handle portion and a brush portion are assembled together to form the electric toothbrush.

In FIG. 1 through FIG. 4, reference numerals 2, 4, and 6 represent a vibrating electric toothbrush, a handle portion, and a brush portion, respectively.

The handle portion 4 is cylindrically shaped and formed from a plastic material. The handle portion 4 is defined with an engaging protuberance portion 8 at one end 4a, i.e., at an engagement location of the handle portion 4. The handle portion 4 further has a cap 10 engaged therewith at the other end 4b. The cap 10 is provided with a switching function.

Figure 4:
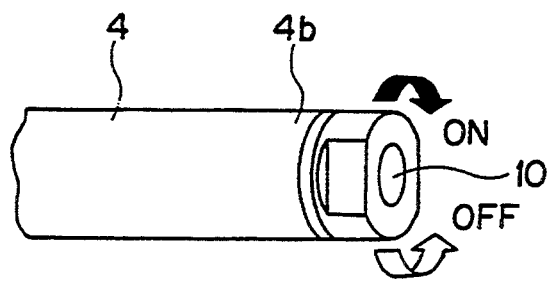
FIG. 4 is a schematic perspective view showing a cap of the electric toothbrush.

Referring now to FIG. 4, the switching function of the cap 10 renders a switch "on" when the cap 10 is turned to the right or clockwise (see the black arrow in FIG. 4). On the other hand, the switching function renders the switch "off" when the cap 10 is backed off by being turned to the left or counterclockwise (see the hollow arrow in FIG. 4).

The handle portion 4 houses an electrically operated motor 12, a heavy eccentric mass 16 disposed offset on a revolving shaft 14 of the motor 12, and a dry battery 18 of size, for example, AAA.

When the motor 12 is driven into rotation, the eccentric heavy mass 16 produces vibration as a result of eccentric displacement of the mass center from the axis of the revolving shaft 14. The vibrating toothbrush 2 is designed to utilize such vibration for brushing.

The brush portion 6 has bristles 20 affixed at one end 6a, while having an engagement hole portion 22 defined at the other end 6b. The bristles 20 are made of pig fur or other linear plastic material.

The brush portion 6, which is defined with the engagement hole portion 22 of a circular cross-section at the end 6b, is a least partly fabricated from a resilient material so as to allow the engaging protuberance portion 8 to be pressed into the engagement hole portion 22. To this end, the engaging protuberance portion 8, which is provided at the engagement location of the handle portion 4, is fabricated from a material stiffer than that of the brush portion 6 defined with the engagement hole portion 22, in order to securely hold the brush portion 6 after the engaging protuberance portion 8 is driven into the engagement hole portion 22.

Figure 5:
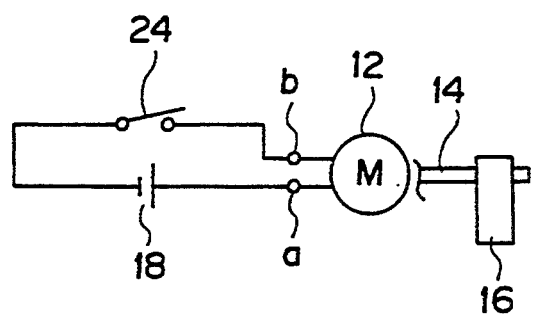
FIG. 5 is a schematic circuit diagram of the electric toothbrush.

Next, a brief description will be provided in connection with an electric circuit of the electric toothbrush 2. As can be seen from FIG. 5, a switch 24 is coupled at one end to a terminal "a" of the motor 12 via the dry battery 18, while being connected at the other to a terminal "b" of the motor 12.

Predeterminations are made as to the respective weights of the electric toothbrush 2 and the eccentric heavy mass 16 as well as the position of the center of gravity of the eccentric heavy mass 16. In accordance with the predetermined conditions, an output of the motor 12 is established within a range of about 6,000 to about 8,000 rpm.

To be specific, a motor conforming to a specification of 1.5 volts and 7,000 rpm is used as the motor 12. A vibration frequency ranging from about 6,000 to about 8,000 rpm, for example, some 7,000 rpm is used. Just for reference, a determination is made as to whether a speed of the motor 12 is specified as 7,000 rpm, in light of the motor coil diameter, the number of times of winding, and the voltage.

Reference numeral 26 represents a tooth growing in the human mouth.

Next, the operation of the present invention will be described.

When an electric toothbrush 2 is used to brush the teeth, the cap 10 of the toothbrush 2 is turned to render the switch 24 "on" so as to drive motor 12 into revolution at about 7,000 rpm. This driving force rotates the heavy eccentric mass 16, thereby producing a vibration of some 7,000 rpm.

Then, the vibration of about 7,000 rpm is conducted to tips of bristles 20. Tooth brushing is practiced by the tips of the bristles 20 being held in contact with the tooth 26.

Figure 6:
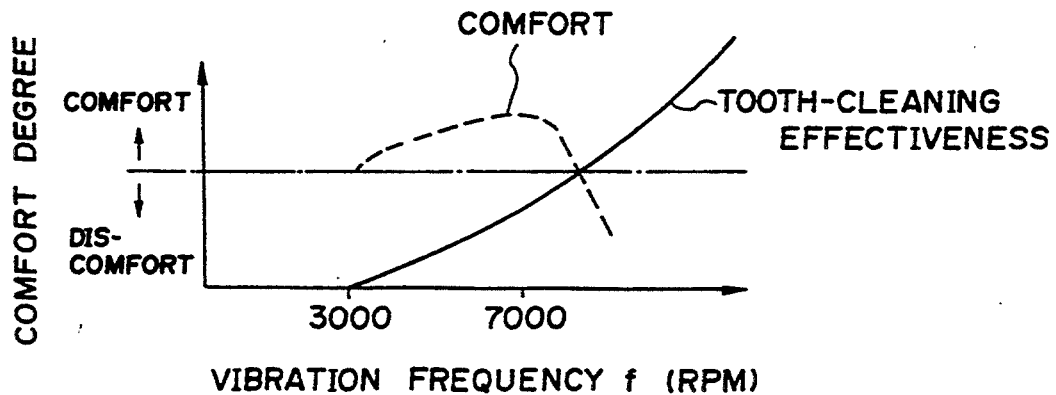
FIG. 6 is a graph, illustrating one relationship between vibration frequency and comfort degree and another relationship between vibration frequency and tooth-cleaning effectiveness.

At this time, as illustrated in FIG. 6, the vibration of about 7,000 rpm produced by the actuation of the motor 12 raises the curve indicative of comfort into a region of comfort, thereby ensuring a high degree of comfort to the user.

Figure 7:
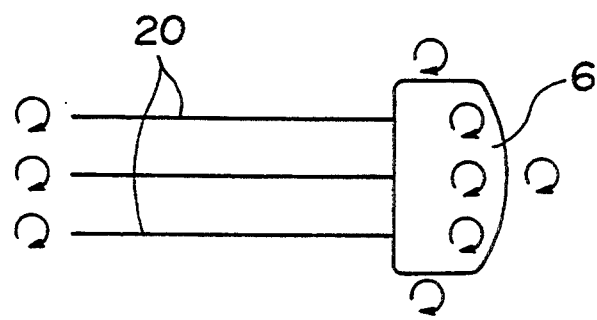
FIG. 7 is a view showing a minute circular motion which is produced by vibration in a plane perpendicular to an axial direction of the brush portion.

Further, as can be seen from FIG. 7, when the vibration of about 7,000 rpm is conducted from the motor 12 to the tips of the bristles 20, the vibration generates a minute circular motion having a diameter of, for example, about 1 mm, which extends in a plane perpendicular to an axial direction of the brush portion 6.

Figure 8:
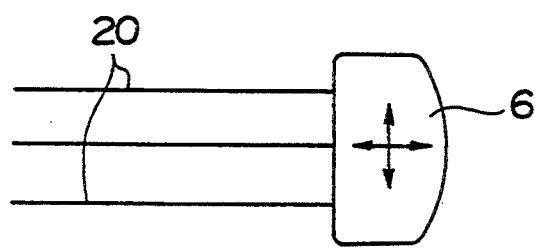
FIG. 8 is a view showing a longitudinal vibration which acts in a direction parallel to axes of filaments of bristles, and a lateral vibration which acts in a direction perpendicular to the axes of the same filament.
Figure 9:
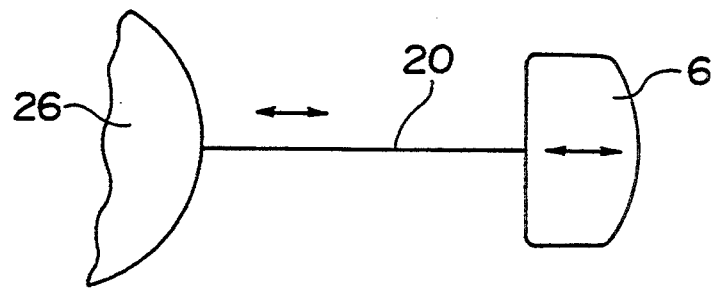
FIG. 9 is a view showing the longitudinal vibration.
Figure 10:
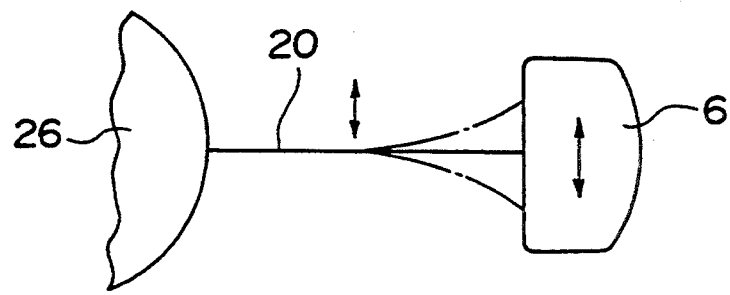
FIG. 10 is a view showing the lateral vibration.

Referring to FIG. 8, the vibration, which has been transmitted to the tips of the bristle 20, are distributed into a longitudinal vibration component and a lateral vibration component. The longitudinal vibration acts in a direction parallel to axes of filaments of the bristles 20, while the lateral vibration acts in a direction perpendicular to the axes of the same filaments. With further reference to FIG. 9, the longitudinal vibration enhances the act of a nudge, with a concomitant increase in the pressing force of the bristles 20. As shown in FIG. 10, the lateral vibration absorbs the bending of bristles 20 by the use of a bias motion.

The above arrangement is advantageous in practical use because when a vibration frequency of the electric toothbrush 2 is set at about 7,000 rpm, a high degree of comfort can be provided as the curve indicative of comfort is raised, as shown in FIG. 6. As a result, a feeling of discomfort which would otherwise occur during brushing is eliminated or minimized.

Furthermore, as can be seen from FIG. 6, the use of the electric toothbrush 2, in which the vibration frequency of about 7,000 rpm is established for brushing, can achieve improved tooth-cleaning effectiveness in removing plaque, dirt or dust, as compared with conventional toothbrushes. This process can ensure sufficient cleaning effectiveness, contributing to reducing the time for cleaning the teeth. As a result, improved convenience of use is achievable.

Moreover, when the vibration is conducted to the tips of the bristles 20 on the brush portion 6, the vibration can massage the gums concurrently with improving cleaning effectiveness during brushing.

It is to be noted that the present invention is not limited to the above-described embodiment, but is applicable to various changes or modifications.

For example, although the vibration frequency described in the above embodiment of the present invention is set up within the range of about 6,000 to about 8,000 rpm, for example, about 7,000 rpm as an average, any vibration frequency other than some 7,000 rpm can be established within the above-mentioned range in consideration of comfort degree and cleaning effectiveness.

In accordance with the present invention as previously described, predeterminations are made to respective weights of an electric toothbrush and eccentric heavy mass as well as a location of the center of gravity of the eccentric heavy mass. In accordance with the predetermined conditions, an output of the motor is established within a range of about 6,000 through about 8,000 rpm. Next, the motor is actuated to produce a vibration ranging from about 6,000 to about 8,000 rpm which is then conducted to tips of bristles on the brush portion. The vibration generates a minute circular motion in a plane perpendicular to an axial direction of the brush portion. A pressing force acting in an axial direction of the bristles is increased by the circular motion. Consequently, the increased pressing force is utilized to brush the teeth. This process is advantageous in practical use because when a vibration frequency of the electric toothbrush is established at about 7,000 rpm, a high degree of comfort can be provided as the curve indicative of comfort is elevated. As a result, a feeling of discomfort is eliminated which would otherwise occur during brushing. Furthermore, the use of the electric toothbrush, in which the vibration frequency of about 7,000 rpm is established for brushing, can achieve improved tooth-cleaning effectiveness in removing plaque, dirt or dust, as compared with conventional toothbrushes. This process can ensure sufficient cleaning effectiveness, contributing to reducing the time for cleaning the teeth. As a result, improved convenience of use is achievable. Moreover, when the vibration is conducted to the tips of the bristles on the brush portion, the vibration can massage the gums concurrently with improving cleaning effectiveness during brushing.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A tooth-brushing method by means of an electric toothbrush including a handle portion, an electrically operated motor built in said handle portion, a brush portion held in engagement with said handle portion, and a heavy eccentric mass designed to produce vibration upon actuation of said motor, wherein said motor is actuated to bring said brush portion into vibration so that brushing is practiced through the aid of said vibration, said tooth-brushing method comprising the steps of:

predetermining respective weights of said electric toothbrush and said heavy eccentric mass as well as an eccentric location of the center of gravity of said heavy eccentric mass;

establishing an output of said motor at about 7,000 rpm in accordance with the predetermined conditions;

producing a vibration of about 7,000 rpm by actuating said motor;

conducting said vibration to tips of bristles on said brush portion to increase a pressing force acting along an axial direction of said bristles by the use of a minute circular motion which is produced by said vibration in a plane perpendicular to an axial direction of said brush portion; and brushing the teeth by utilizing said increased pressing force.

* * * * *